(12) United States Patent
Fetzer et al.

(10) Patent No.: US 12,241,814 B2
(45) Date of Patent: Mar. 4, 2025

(54) SYRINGE SCREENING DEVICE

(71) Applicant: TAKEDA PHARMACEUTICAL COMPANY LIMITED, Osaka (JP)

(72) Inventors: Chase Fetzer, Lexington, MA (US); Evi Shiakolas, Lexington, MA (US)

(73) Assignee: TAKEDA PHARMACEUTICAL COMPANY LIMITED, Osaka (JP)

( * ) Notice: Subject to any disclaimer, the term of this patent is extended or adjusted under 35 U.S.C. 154(b) by 0 days.

(21) Appl. No.: 18/126,290

(22) Filed: Mar. 24, 2023

(65) Prior Publication Data

US 2023/0304899 A1 Sep. 28, 2023

Related U.S. Application Data

(63) Continuation of application No. 16/268,738, filed on Feb. 6, 2019, now Pat. No. 11,614,381.

(60) Provisional application No. 62/628,378, filed on Feb. 9, 2018.

(51) Int. Cl.
  *G01M 99/00* (2011.01)
  *A61M 5/28* (2006.01)

(52) U.S. Cl.
  CPC ............ *G01M 99/00* (2013.01); *A61M 5/281* (2013.01); *A61M 2209/02* (2013.01)

(58) Field of Classification Search
  CPC .. G01M 99/00; A61M 5/281; A61M 2209/02; A61M 5/20; A61M 2205/58; A61M 2205/583; A61M 39/20; A61M 2005/3101; A61M 2005/3103; A61M 2005/3106; G01B 3/00; G01B 3/02; G01B 3/04; G01B 3/08; G01B 3/22; G01B 3/28; G01B 3/008
  See application file for complete search history.

(56) References Cited

U.S. PATENT DOCUMENTS

| 1,248,340 | A | * | 11/1917 | Kinney | G01B 3/28 33/836 |
|---|---|---|---|---|---|
| 2,175,650 | A | | 7/1937 | Fred | |
| 4,450,834 | A | | 5/1984 | Fischer | |
| 5,038,600 | A | | 8/1991 | Friedman | |
| 5,899,889 | A | | 5/1999 | Futagawa et al. | |
| 8,722,178 | B2 | | 5/2014 | Ashmead et al. | |

(Continued)

FOREIGN PATENT DOCUMENTS

| EP | 0781567 B1 | 7/1997 |
|---|---|---|
| JP | 2008-122229 A | 5/2008 |
| WO | 2008012611 A2 | 1/2008 |

OTHER PUBLICATIONS

International Search Report and Written Opinion issued in International Application No. PCT/US2019/016761 dated Apr. 18, 2019.

*Primary Examiner* — Son T Le
*Assistant Examiner* — Matthew W. Baca
(74) *Attorney, Agent, or Firm* — Troutman Pepper Locke LLP

(57) ABSTRACT

The present disclosure is directed to a device for screening pre-filled syringes configured to determine whether a stopper position within each syringe falls within an acceptable tolerance prior to final assembly of a syringe into a corresponding autoinjector device, thereby ensuring proper fit of the syringe within the autoinjector device and further ensuring accurate delivery of a desired dose of fluid from the syringe during operation of the autoinjector.

7 Claims, 13 Drawing Sheets

(56) References Cited

U.S. PATENT DOCUMENTS

| | | | |
|---|---|---|---|
| 8,764,703 B2 | 7/2014 | Asai et al. | |
| 9,881,367 B1 * | 1/2018 | Milne | G06T 7/11 |
| 2009/0241644 A1 | 10/2009 | Bonfiglioli | |
| 2009/0313842 A1 * | 12/2009 | Wu | G01B 3/28 |
| | | | 33/556 |
| 2016/0259913 A1 | 9/2016 | Yu et al. | |
| 2017/0342879 A1 | 11/2017 | Lim, Jr. | |
| 2019/0125371 A1 | 5/2019 | Asfora et al. | |

* cited by examiner

Assembly of Pre-filled Syringe into Autoinjector

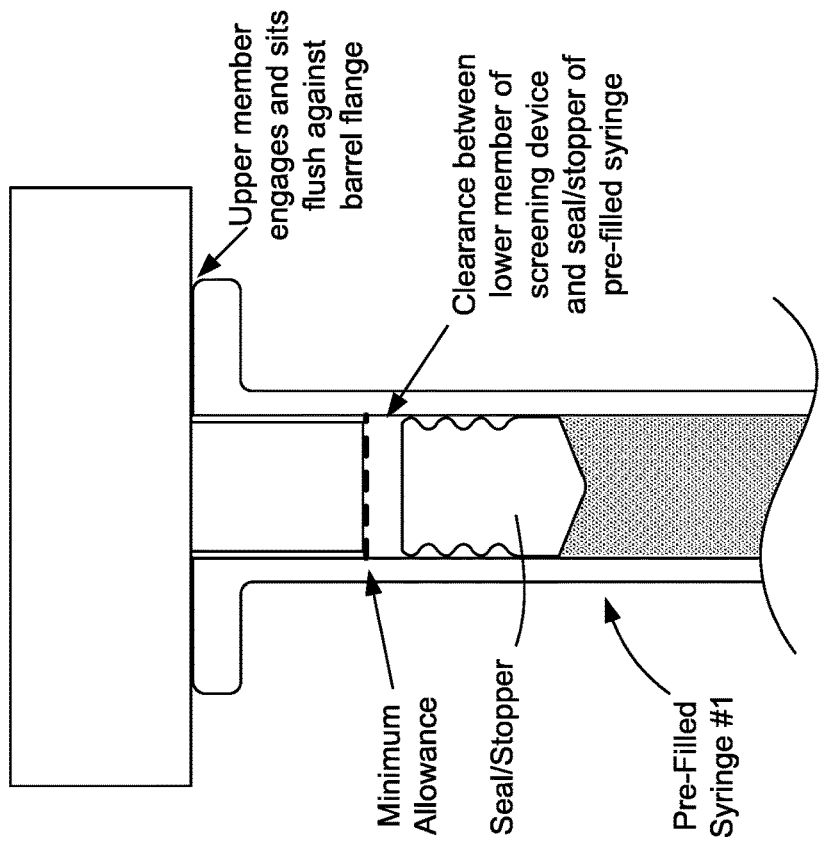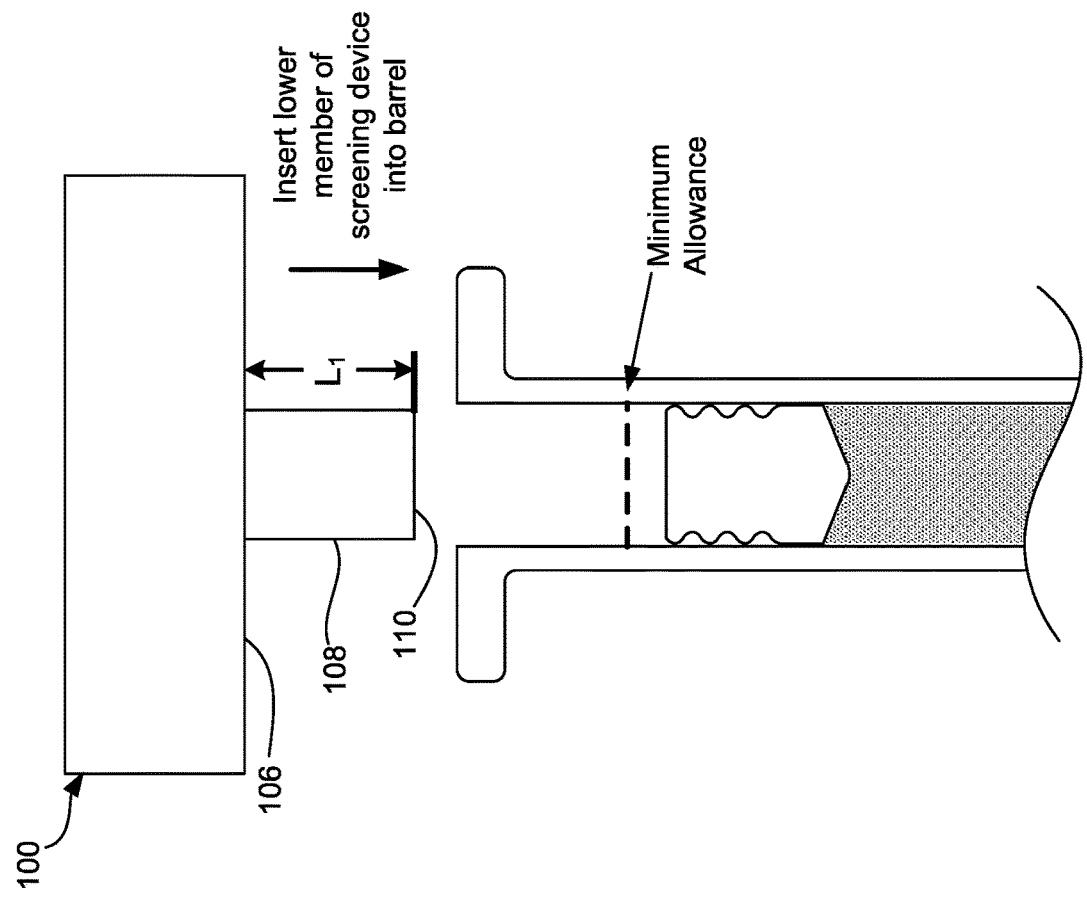

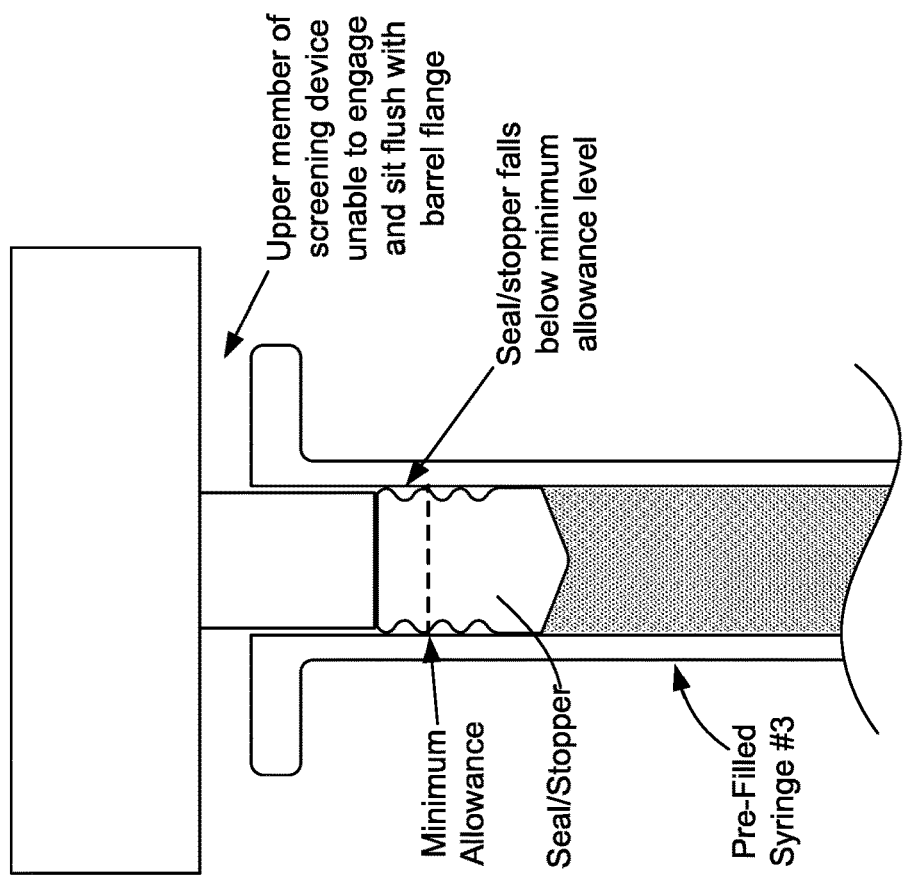
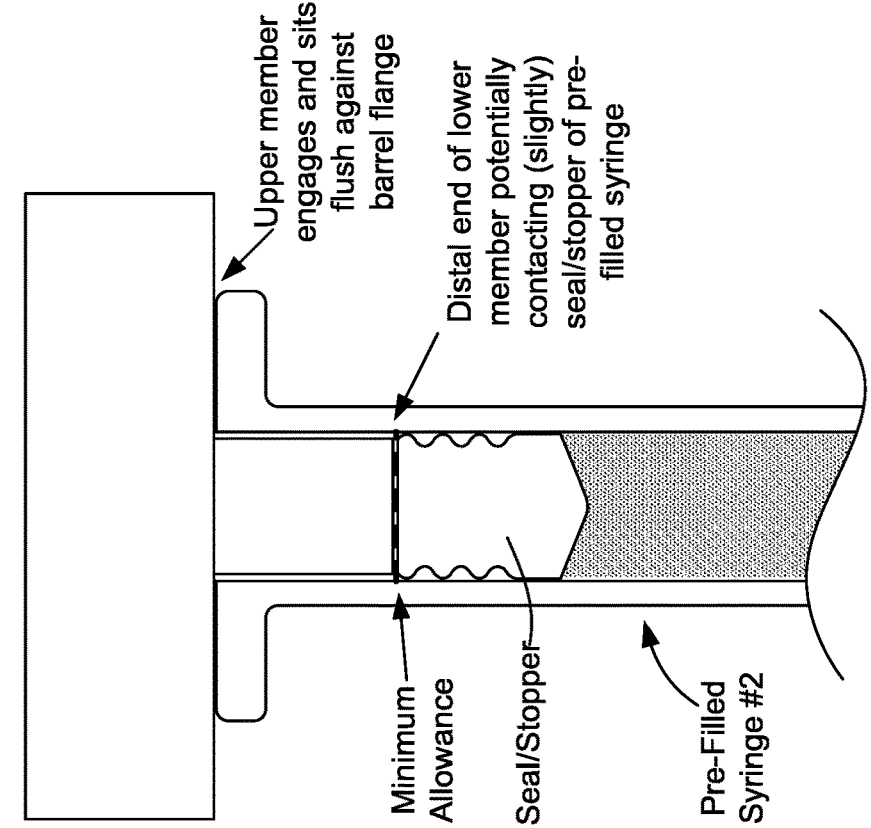
FIG. 9D
FIG. 9C

SYRINGE SCREENING DEVICE

CROSS-REFERENCE TO RELATED APPLICATIONS

This application is a continuation of, and claims priority under 35 U.S.C. § 120 to, U.S. patent application Ser. No. 16/268,738, filed on Feb. 6, 2019, which claims benefit to U.S. Provisional Application No. 62/628,378, filed on Feb. 9, 2018. The entire contents of these applications are incorporated by reference herein in their entirety.

FIELD

The present disclosure relates generally to quality control measures for medical devices. In particular, the present disclosure is directed to a device for screening pre-filled syringes to determine whether the pre-filled syringes meet specific manufacturing specifications prior to loading of the pre-filled syringes into corresponding autoinjector devices.

BACKGROUND

An autoinjector device is an injection device designed to facilitate automated delivery of a dose of drug to a patient. By design, autoinjectors are relatively easy to use and are intended for self-administration by patients or administration by the medically untrained. For example, the design of an autoinjector is relatively simple, consisting generally of at least a housing enclosing a chamber filled with a dose of a drug and a needle in fluid communication with the chamber, which may be delivered via a spring-loaded plunger rod. Upon actuation of a release mechanism (i.e., user pushing button or lever, or simply pressing the housing against the desired injection site), the needle is inserted into the injection site and the spring-loaded plunger rod is automatically released for delivering the drug from the chamber.

Some autoinjector devices have a custom designed chamber incorporated into the housing itself. While an integrated chamber may allow for a more compact size, such an autoinjector as whole must be subjected to more rigorous regulatory control as compared with an autoinjector device containing a standard pre-filled syringe, which will have already obtained regulatory approval. Accordingly, many autoinjectors are manufactured around pre-filled syringes, such that any given autoinjector can be customized in both shape and size so as to accommodate a specific size of pre-filled syringe depending on the desired dosage of any given drug. For example, some autoinjector devices are designed to accommodate 1 ml long pre-filled glass or polymer syringes, while some autoinjector devices are designed to accommodate alternative syringe sizes (e.g. 2.25 ml or greater).

In many instances, autoinjector devices and pre-filled syringes are produced separately from one another and by different manufacturers. For example, one manufacturer may produce and assemble the structural components of the autoinjection device itself (i.e., the housing, a needle if not included on the pre-filled syringe, a spring, spring-release mechanism, a plunger rod for contacting and pushing a corresponding stopper in the pre-filled syringe, etc.) while another manufacturer produces the pre-filled syringes (i.e., syringe filled with a dose of drug and sealed with a stopper). Accordingly, the final, ready-to-use autoinjector consists of a pre-filled syringe loaded within the separate autoinjector housing.

While current autoinjector designs may be attractive from both a cost standpoint and the ease of manufacture, such designs have shortcomings. For example, during the manufacturing process, specific dimensions and/or geometries of the autoinjector device components must be maintained within a given tolerance range to ensure that the corresponding pre-filled syringe fits within the autoinjector housing and functions as intended. The same holds true during the manufacturing of pre-filled syringes, in which the amount of fluid drug provided within the syringe barrel, as well as the location of the stopper sealing the fluid within syringe barrel, must be maintained within a given tolerance range. However, as a result of natural variation that occurs during any given manufacturing process, particularly when a product has parts produced separately from one another and by different manufacturers, it is inevitable that one or more autoinjector device components and/or one or more pre-filled syringes falls outside of a given tolerance range, and thus presents issues during the final assembly.

For example, if dimensions of the autoinjector components securing the prefilled syringe fall outside of particular standards, then the components may be unable to fully accommodate a pre-filled syringe (i.e., if the component is too small) or, in the event that the component is too large, then the pre-filled syringe may not be properly secured within the housing and in proper engagement with the internal components, which may result in a defective autoinjector. Furthermore, even if the pre-filled syringe is able to be loaded within the autoinjector components to thereby resemble a final, ready-to-use autoinjector, improper placement of the stopper within the barrel of the pre-filled syringe (as a result of natural variance during the manufacturing process) can result in a defective autoinjector due to an unintended leakage of the fluid drug from the needle prior to use. In particular, if the stopper of the pre-filled syringe falls outside of a given tolerance (i.e., is not placed within a given location along a length of the syringe barrel), then, upon loading the pre-filled syringe within the autoinjector housing, the corresponding plunger rod of the autoinjector device may engage and move the stopper during assembly, thereby forcing some of the fluid drug to leak out of the syringe upon removal of the cap of the autoinjector. This leakage of fluid may therefore result in an incomplete dose of drug administered during use of the autoinjector as a result of some fluid loss due to leakage, which can lead to ineffective treatment and potentially serious side effects. The inadvertent fluid leakage may be particularly troublesome when an exact dose of drug is required for any particular treatment to be effective. Furthermore, inadvertent leakage can result in a lack of apparent quality at the Point-of-Care, or use by the patient, were they to experience leakage upon removal of the cap of the autoinjector.

SUMMARY

The present invention is directed to a screening device for screening pre-filled syringes prior to loading of the pre-filled syringes into corresponding autoinjector devices for subsequent use. The screening device is used for determining whether the pre-filled syringes meet specific manufacturing specifications to ensure proper fit of the pre-filled syringes within the autoinjector devices so as to further ensure proper assembly of the prefilled syringe into the autoinjector and prevent leakage of fluid contents from the syringe upon removal of the cap. In particular, the screening device is used for determining whether the seal or stopper (hereinafter referred to as "stopper") positioned in the syringe barrel falls within an acceptable tolerance prior to final assembly of the pre-filled syringe into the corresponding autoinjector device. The screening of pre-filled syringes ensures that only those pre-filled syringes that meet the requisite standards (i.e., syringes including stoppers positioned within the acceptable tolerance range) are passed along for final assembly with corresponding autoinjector devices, thereby reducing the risk of introducing a leaking, and potentially defective, autoinjector into the market.

The screening device of the present disclosure has a relatively simple, yet effective design for determining proper placement of stoppers in a plurality of pre-filled syringes. The screening device generally comprises a body including an upper member and a lower member extending therefrom. The upper member and the lower member may each have a cylindrical shape, wherein the upper member has a diameter greater than a diameter of the syringe barrel while the lower member has a diameter less than a diameter of the syringe barrel so as to allow the lower member to be inserted into an open proximal end of a pre-filled syringe barrel. Upon placement of the lower member into the open proximal end of a syringe barrel, the upper member, due to the larger diameter, is adapted to engage the open proximal end and abut a flange portion of the open proximal end. Placement of the screening device within the open proximal end allows for determination of whether the stopper is positioned a minimum distance from the proximal end which dictates whether the pre-filled syringe passes or fails the screening.

The minimum distance is a predetermined tolerance factor related to a specific location along a length of syringe barrel to which a plunger rod from a corresponding autoinjector device, which has been manufacturer specified to accommodate the pre-filled syringes, may extend when the pre-filled syringe is loaded into the autoinjector for use. If a stopper is determined to be positioned at or greater than the minimum distance (i.e. further inside the syringe barrel), then it is determined that the pre-filled syringe passes the screening procedure, thereby ensuring that a plunger rod from a corresponding autoinjector has sufficient clearance when the pre-filled syringe is loaded into the autoinjector and the plunger rod will not prematurely contact the stopper prior to firing of the autoinjector. If, however, the stopper is determined to be positioned less than the minimum distance from the open proximal end (i.e., the stopper is too close to the open proximal end of the barrel), then it is determined that the pre-filled syringe fails the screening test and is subsequently taken out of circulation to ensure that the defective pre-filled syringe is not passed on for subsequent loading into an autoinjector, which could otherwise result in a potentially defective autoinjector in that it could leak fluid contents therefrom.

In one embodiment, the lower member of the screening device may be in a fixed position relative to the upper member (i.e., the lower member does not move relative to the upper member). For example, in some embodiments, the upper and lower members may be integrally formed with one another, while in other embodiments, the upper and lower members may be formed separately and then secured to one another in a fixed position via adhesive, ultrasonic welding, or the like. In such embodiments, the lower member has a length measured from a bottom surface of the upper member, from which the lower member extends, to a distal end of the lower member. The length of the lower member is approximately equal to the predetermined minimum distance (i.e., specific distance along a length of syringe barrel to which a plunger rod from a corresponding autoinjector device extends when the pre-filled syringe is loaded into the autoinjector). Accordingly, upon insertion of the lower member into the open proximal end of a pre-filled syringe, the distal end of the lower member will either make contact with the stopper in the barrel (indicating that the stopper position is less than the minimum distance and fails the screening procedure) or will not make contact with the stopper (indicating that the stopper position is greater than the minimum distance and passes the screening procedure).

For example, in the event that the distal end of the lower member makes contact with a stopper that is positioned below the minimum distance, the entire length of the lower member will be prevented from being received within the syringe barrel due to the resistance encountered from the stopper. In turn, the upper member will sit proud relative to the open proximal end of the syringe barrel (i.e., the upper member will not make contact and sit flush with the open proximal end), thereby providing a visual indication to the screener that the pre-filled syringe fails the screening procedure. In the event that the entire length of the lower member is able to be received within the syringe barrel as a result of the stopper position being greater than the minimum distance, then the upper member will make contact and sit flush with the open proximal end, thereby providing a visual indication to the screener that the pre-filled syringe passes the screening procedure.

In other embodiments, the lower member may be movably coupled to the upper member such that the lower member can move relative to the upper member upon encountering resistance from the stopper when a screener inserts the lower member into the syringe barrel. It should be noted that, in such embodiments, the screening device, particularly the lower member body, includes a relatively lightweight material (e.g., lightweight plastic) to ensure that the lower member body does not move the stopper from its position in the barrel. In particular, the upper member may include a central bore for receiving the lower member which may generally translate along a longitudinal axis of the upper member between various positions that can provide a screener with visual indications as to whether the pre-filled syringe passes or fails the screening procedure. For example, the lower member may resemble a floating pin, in that the lower member includes an elongate body (i.e., a rod or pin) received within the central bore of the upper member. The lower member body includes a proximal end including a flanged top adapted to rest upon a top surface of the upper member and maintain the lower member body within the central bore of the upper member and an opposing distal end for contacting the stopper during the screening procedure.

The floating pin screening device can provide a visual indication to a screener as to whether the pre-filled syringe passes or fails the screening procedure simply based on whether the flanged top remains flush against the top surface of the upper member or pops up and sits proud relative to the top surface of the upper member. For example, in one embodiment, a single visual indicator (i.e., color, insignia, marking) is provided along a length of the proximal end of the lower member, immediately adjacent to the flanged top, indicating failure of the screening procedure. For example, the single visual indicator may be the color red or may have text reading "FAIL", or the like. The single visual indicator is only visible to a screener if the flanged top pops up and sits proud. Accordingly, in this embodiment, the specific length of the lower member body (that extends from the bottom surface of the upper member when the flanged top is sitting flush with the top surface of the upper member) is approximately equal to the predetermined minimum distance. Thus, if the distal end of the lower member body makes contact with a stopper that is positioned below the minimum distance, the resistance encountered from the stopper will cause the lower member body to translate relative to the upper member (which is abutting the open proximal end of the syringe barrel), thereby causing the flanged top to sit proud relative to the top surface of the upper member and exposing the single visual indicator to indicate failure. In the event that the entire length of the lower member body is able to be received within the syringe barrel as a result of the stopper position being greater than the minimum distance, then the flanged top will remain flush with the top surface of the upper member, thereby indicating to the screener that the pre-filled syringe passes the screening procedure.

In another embodiment, two visual indicators are provided along a length of the proximal end of the lower member, including a first visual indicator immediately adjacent to the flanged top and indicating passing of the screening procedure, and a second visual indicator adjacent to the first visual indicator and indicating failure of the screening procedure. For example, the first visual indicator may be the color green and/or may have text reading "PASS", or the like, while the second visual indicator may be the color red and/or may have text reading "FAIL". In this embodiment, the specific length of the lower member body (that extends from the bottom surface of the upper member when the flanged top is sitting flush with the top surface of the upper member) is greater than the predetermined minimum distance so as to account for a length of the first visual indicator provided on the proximal end of the lower member and allow the flanged top to sit proud and expose the first visual indicator to indicate passage of the pre-filled syringe.

For example, unlike other embodiments in which a flanged top sitting flush with the upper member indicates passing of the pre-filled syringe, the two-indicator screening device requires the flanged top to sit proud to expose the first visual indicator to indicate passing of the pre-filled syringe. Thus, upon the distal end of the lower member body contacting a stopper that is positioned at or above the minimum distance, the lower member body translates relative to the upper member (which is abutting the open proximal end of the syringe barrel), thereby causing the flanged top to sit proud relative to the top surface of the upper member and exposing the first visual indicator to indicate that the pre-filled syringe passes the screening procedure. In the event that the stopper is positioned below the minimum distance, the flanged top will continue to rise to then expose the second visual indictor to indicate failure.

Accordingly, the screening devices of the present disclosure provide a relatively simple, yet effective design for determining proper placement of stoppers in a plurality of pre-filled syringes to ensure that only those pre-filled syringes that meet the requisite standards (i.e., syringes including stoppers positioned within the acceptable tolerance range) are passed along for final assembly with corresponding autoinjector devices, thereby reducing the risk of introducing a potentially defective autoinjector into the market.

BRIEF DESCRIPTION OF THE DRAWINGS

Features and advantages of the claimed subject matter will be apparent from the following detailed description of embodiments consistent therewith, which description should be considered with reference to the accompanying drawings.

FIG. 9A is an enlarged side view, partly in section, illustrating placement of the screening device of FIG. 6 relative to an open proximal end of a pre-filled syringe.

FIGS. 9B-9D are enlarged side views, partly in section, illustrating passing and failing of the pre-filled syringe based on physical positioning of the screening device as a result of the position of the stopper within the pre-filled syringe.

For a thorough understanding of the present disclosure, reference should be made to the following detailed description, including the appended claims, in connection with the above-described drawings. Although the present disclosure is described in connection with exemplary embodiments, the disclosure is not intended to be limited to the specific forms set forth herein. It is understood that various omissions and substitutions of equivalents are contemplated as circumstances may suggest or render expedient.

DETAILED DESCRIPTION

The present invention is directed to a screening device for screening pre-filled syringes prior to loading of the pre-filled syringes into corresponding autoinjector devices for subsequent use. The screening device is used for determining whether the pre-filled syringes meet specific manufacturing specifications to ensure proper fit of the pre-filled syringes within the autoinjector devices so as to further ensure proper assembly of the prefilled syringe into the autoinjector and prevent leakage of fluid contents from the syringe upon removal of the cap. In particular, the screening device is used for determining whether the seal or stopper (hereinafter referred to as "stopper") positioned in the syringe barrel falls within an acceptable tolerance prior to final assembly of the pre-filled syringe into the corresponding autoinjector device. The screening of pre-filled syringes ensures that only those pre-filled syringes that meet the requisite standards (i.e., syringes including stoppers positioned within the acceptable tolerance range) are passed along for final assembly with corresponding autoinjector devices, thereby reducing the risk of introducing a leaking, and potentially defective, autoinjector into the market.

Figure 1:
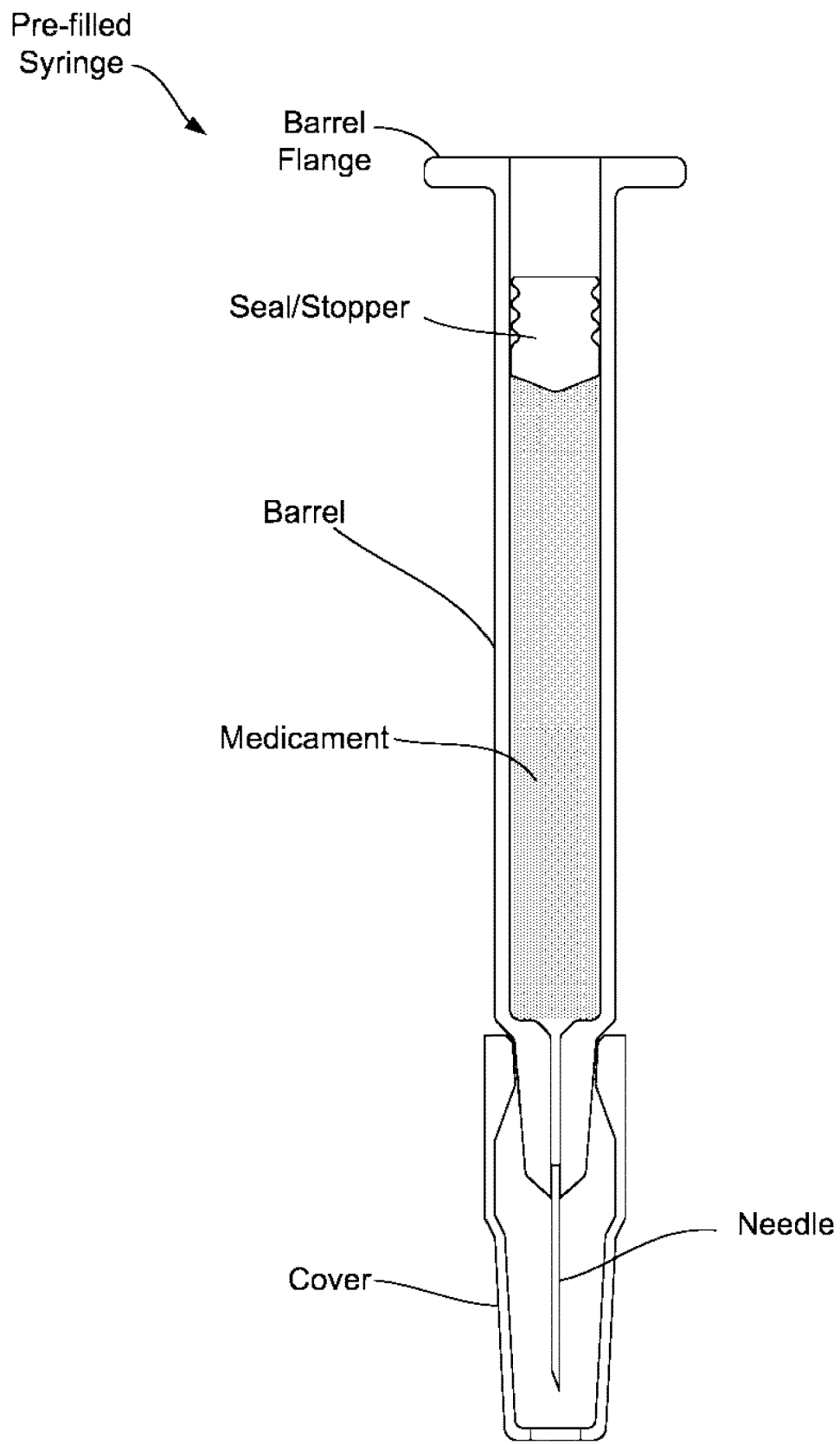
FIG. 1 is cross-sectional view of an exemplary pre-filled syringe suitable for screening with the screening device consistent with the present disclosure.
Figure 2:
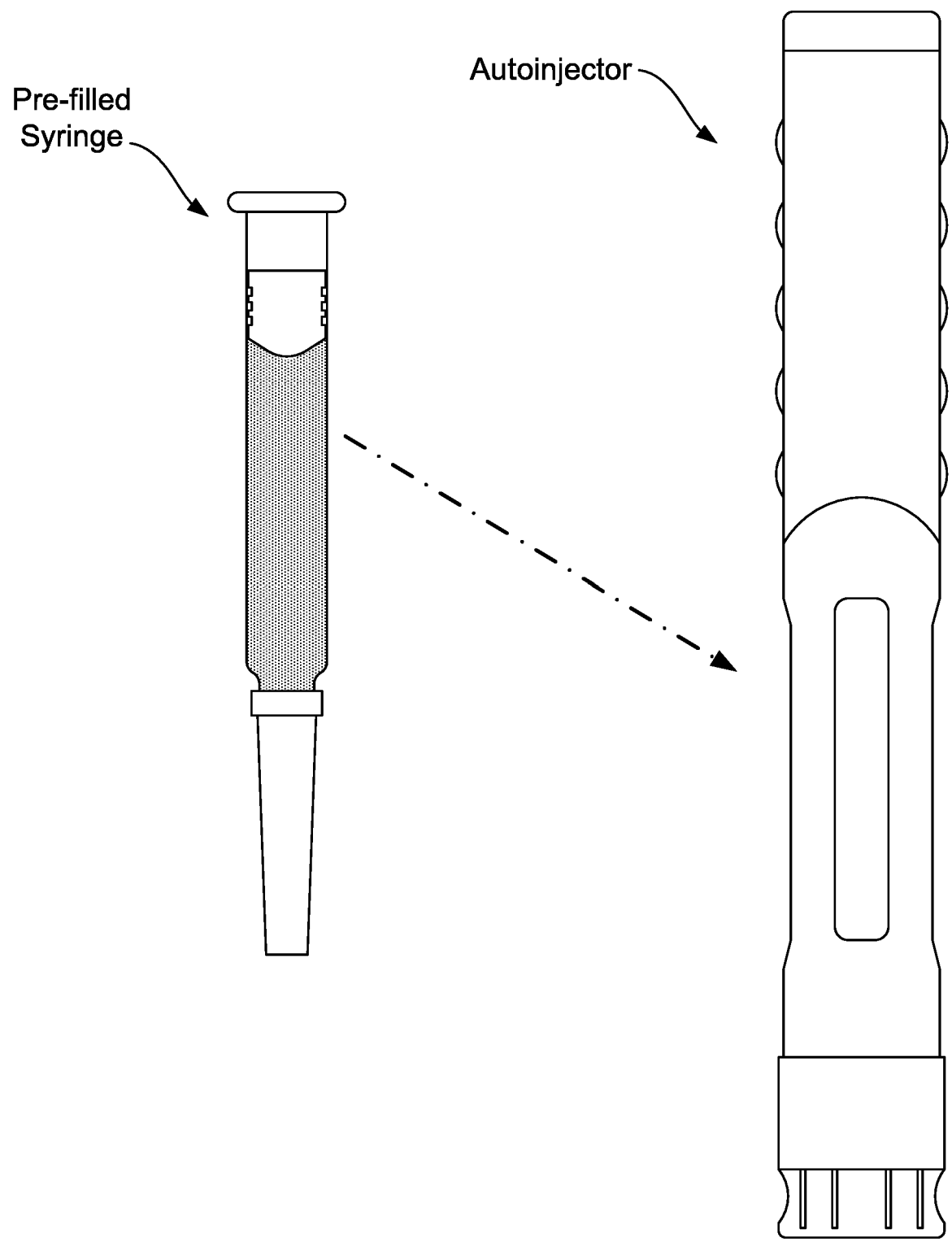
FIG. 2 is a side view of view illustrating preassembly of an exemplary pre-filled syringe and a corresponding autoinjector configured to accommodate the pre-filled syringe.

FIG. 1 is cross-sectional view of an exemplary pre-filled syringe suitable for screening with the screening device consistent with the present disclosure and FIG. 2 is a side view illustrating preassembly of an exemplary pre-filled syringe and a corresponding autoinjector configured to accommodate the pre-filled syringe. As previously described, some autoinjector devices can be manufactured around pre-filled syringes, such that any given autoinjector can be customized in both shape and size so as to accommodate a specific size of pre-filled syringe depending on the desired dosage of any given drug. In many instances, autoinjector devices and pre-filled syringes are produced separately from one another and by different manufacturers. For example, the autoinjector illustrated herein may be the YPSOMATE 1 mL autoinjector, offered by Ypsomed AG (Burgdorf, Switzerland) and the pre-filled syringe illustrated herein may be a standard 1 ml long pre-filled glass or polymer syringe offered by Vetter Pharma-Fertigung GmbH & Co. KG (Ravensburg, Germany). Accordingly, the final, ready-to-use autoinjector, as illustrated in FIG. 3, consists of a pre-filled syringe loaded within the separate autoinjector housing.

As shown, a standard pre-filled syringe may generally consist of a syringe barrel for receiving an amount (generally a single dose) of a medicament. A seal or stopper (also referred to as a piston) is placed within the barrel after the filling process so as to contain the fluid within. The stopper further serves as a means of expelling the fluid medicament from the barrel, through a needle coupled thereto and in fluid communication with the barrel, when force is applied to the stopper. In particular, the pre-filled syringes further include an open proximal end for receiving a rod or other mechanical device for contacting and applying force to the stopper to cause movement thereof and result delivery of the fluid drug from the barrel. The pre-filled syringe may further include a safety cover or cap for shielding the needle so as to prevent inadvertent needle sticks during handling and maintain sterility of the fluid contacting path.

Figure 3:
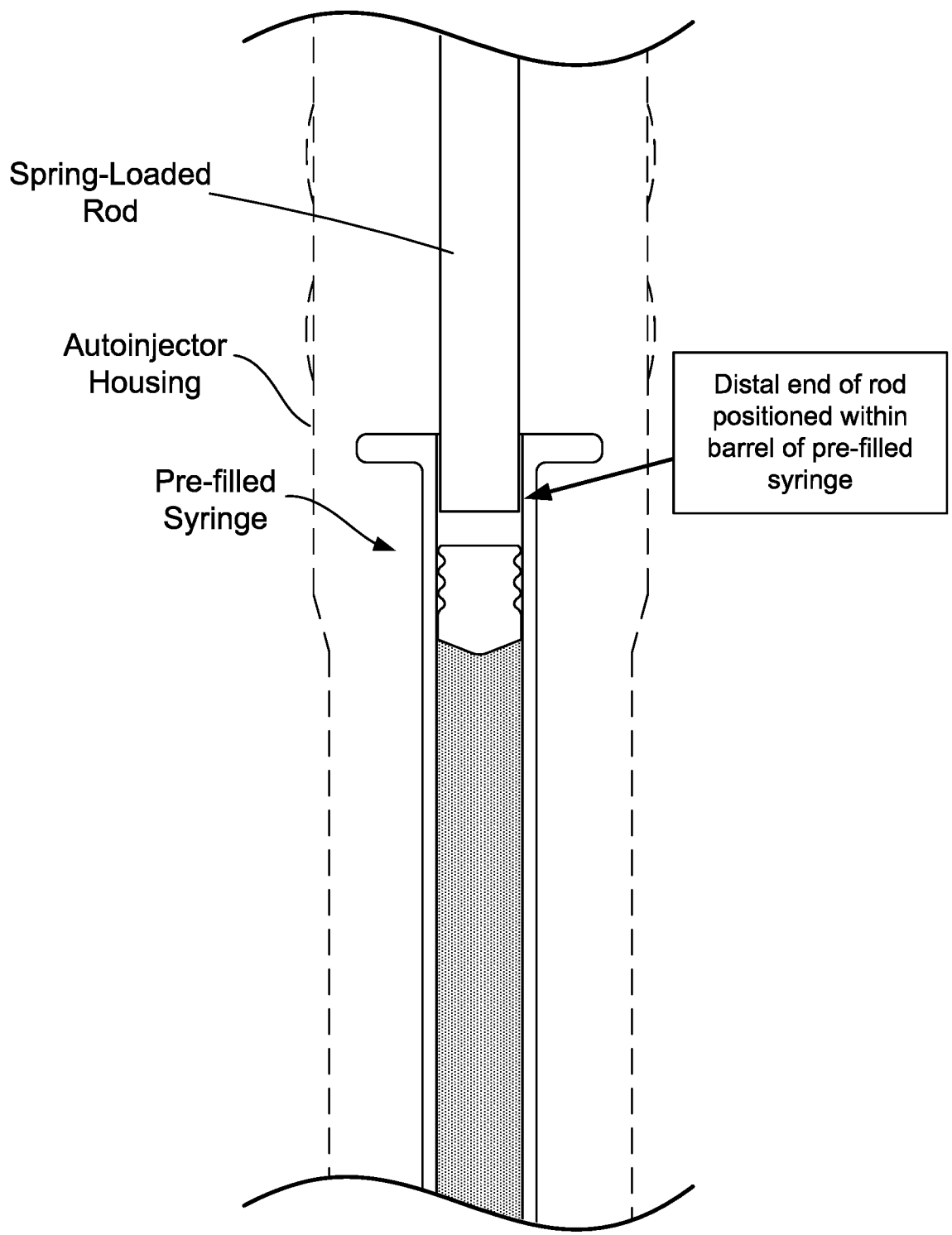
FIG. 3 is side view, partly in section, of the pre-filled syringe loaded into the corresponding autoinjector.
Figure 4:
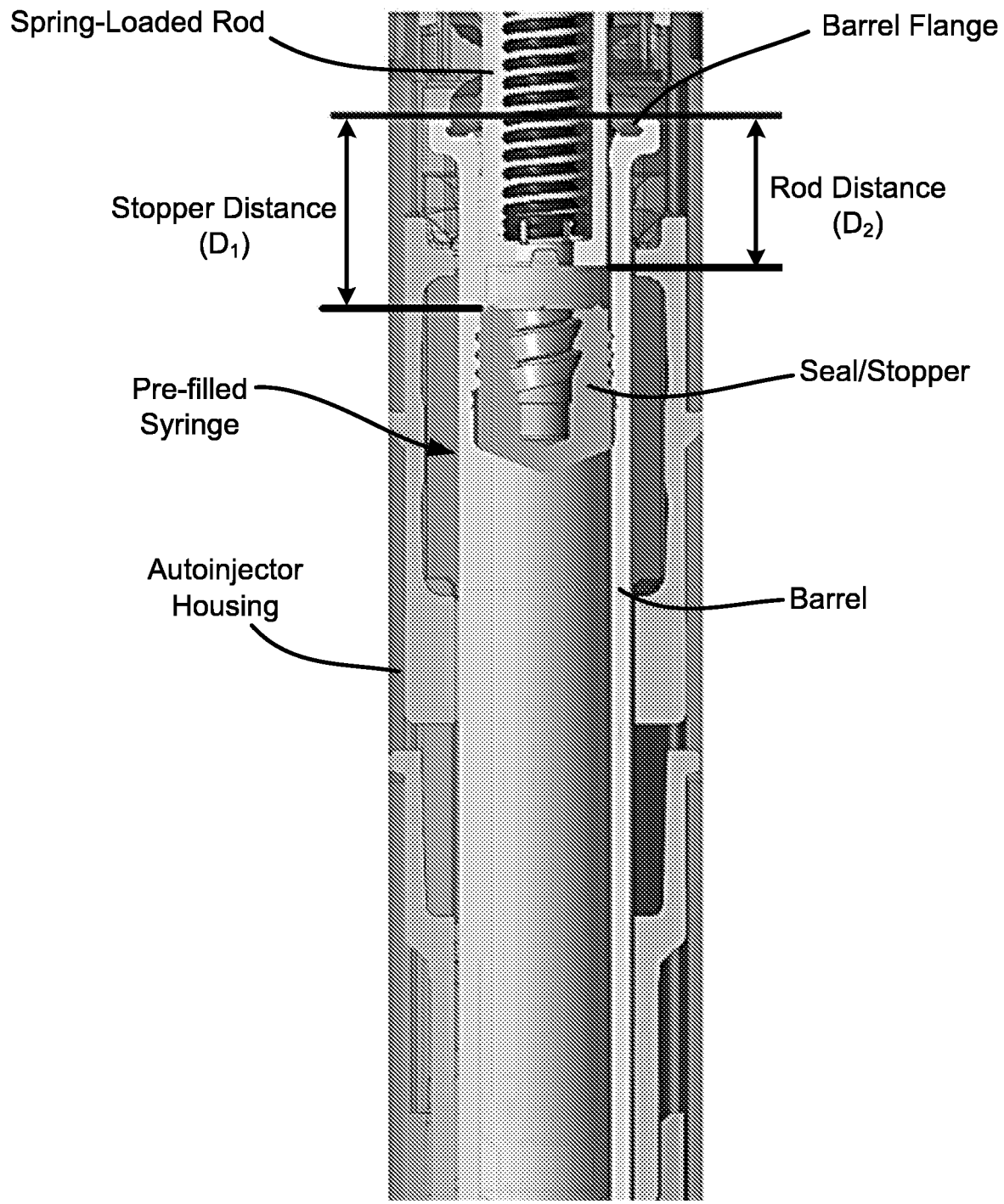
FIG. 4 is a cross-sectional view of an exemplary pre-filled syringe loaded into a corresponding autoinjector device illustrating various internal components of the autoinjector device and the positioning of the spring-loaded rod relative to the pre-filled syringe.
Figure 5:
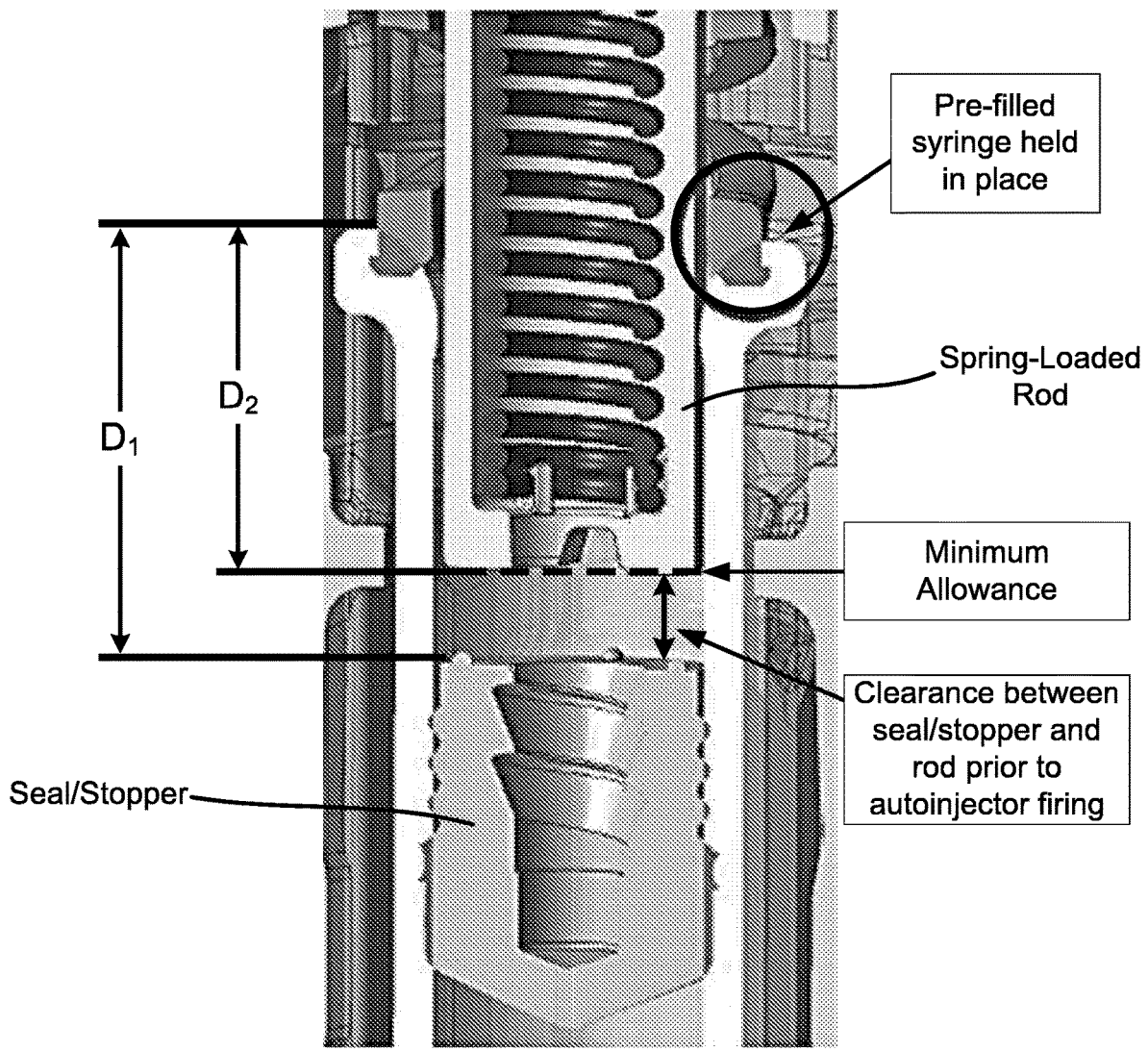
FIG. 5 is an enlarged cross-sectional view of the loaded pre-filled syringe and autoinjector device components relative to one another.

FIG. 3 is side view, partly in section, of the pre-filled syringe loaded into the corresponding autoinjector, and FIG. 4 is a cross-sectional view of an exemplary pre-filled syringe loaded into a corresponding autoinjector device illustrating various internal components of the autoinjector device. FIG. 5 is an enlarged cross-sectional view of the loaded pre-filled syringe and autoinjector device components relative to one another. The autoinjector device is an injection device designed to facilitate automated delivery of a dose of drug to a patient. The design of an autoinjector is relatively simple, consisting generally of at least a housing configured to receive and enclose the pre-filled syringe therein, and a spring-loaded rod aligned with the syringe barrel and the stopper. Upon actuation of a release mechanism (i.e., user pushing button or lever, or simply pressing the housing against the desired injection site), the spring-loaded rod is released and engages the stopper, thereby advancing the stopper, due to the force from the loaded spring, through the barrel and causing delivering the fluid through the needle into the injection site.

The autoinjector device is manufactured around pre-filled syringes, such that any given autoinjector device can be customized in both shape and size so as to accommodate a specific size of pre-filled syringe depending on the desired dosage of any given drug. For example, some autoinjector devices are designed to accommodate 1 ml long pre-filled glass or polymer syringes, while some autoinjector devices are designed to accommodate alternative syringe sizes (e.g. 2.25 ml or greater).

As shown, shown in FIG. 4, for example, upon loading the pre-filled syringe into the autoinjector housing, the spring-loaded plunger rod is generally aligned with the syringe barrel and, in some instances, extends into the open proximal end of the barrel. Accordingly, specific dimensions and/or geometries of the autoinjector device components must be maintained within a given tolerance range to ensure that the corresponding pre-filled syringe fits within the autoinjector housing and functions as intended. The same holds true during the manufacturing of pre-filled syringes, in which the amount of fluid drug provided within the syringe barrel, as well as the location of the stopper sealing the fluid within syringe barrel, must be maintained within a given tolerance range. For example, by design, the spring-loaded plunger rod of the autoinjector device may be consistently manufactured to have a specific length when in a pre-firing configuration (rod is retracted and ready to fire). Accordingly, upon loading the pre-filled syringe into the autoinjector housing and into alignment with the spring-loaded rod, the rod may consistently reside within the syringe barrel a certain distance. For example, as shown in FIGS. 4 and 5, the stopper may be a distance $D_1$ from the barrel flange, while the distal-most end of the plunger rod may be a distance $D_2$ from the barrel flange, wherein there is a clearance between distance $D_1$ and $D_2$. Accordingly, it is important that the stopper of any given pre-filled syringe be positioned at a distance (hereinafter referred to as "minimum distance") from the barrel flange that is greater than the distance (distance $D_2$) that the distal-most end of the plunger rod will reside when the pre-filled syringe is loaded into the autoinjector device.

The minimum distance is a predetermined tolerance factor related to a specific location along a length of syringe barrel to which a plunger rod from a corresponding autoinjector device, which has been manufacturer specifically to accommodate the pre-filled syringes, may extend when the pre-filled syringe is loaded into the autoinjector for use. The minimum distance will vary, as it is based on the specific autoinjector device and the specific pre-filled syringes to be loaded into the autoinjector device. In some embodiments, the minimum distance is approximately 8.0 mm. In other embodiments, the minimum distance is approximately 8.46 mm. Yet still, in other embodiments, the minimum distance may be less than 8.0 mm or greater than 8.46 mm.

As a result of natural variation that occurs during any given manufacturing process, particularly when a product has parts produced separately from one another and by different manufacturers, it is inevitable that one or more autoinjector device components and/or one or more pre-filled syringes falls outside of a given tolerance range, and thus presents issues during the final assembly. For example, if a stopper is positioned at or greater than the minimum distance, then the plunger rod has sufficient clearance when the pre-filled syringe is loaded into the autoinjector and the plunger rod will not prematurely contact the stopper prior to firing of the autoinjector, thereby ensuring that the autoinjector function properly as intended. If, however, the stopper is positioned less than the minimum distance from the open proximal end (i.e., the stopper is too close to the open proximal end of the barrel), then, upon loading the pre-filled syringe within the autoinjector housing, the plunger rod may engage and move the stopper during assembly, thereby forcing some of the fluid drug to leak out of the syringe prior to use of the autoinjector. This leakage of fluid may therefore result in an incomplete dose of drug administered during use of the autoinjector as a result of some fluid loss due to leakage, which can lead to ineffective treatment and potentially serious side effects. The inadvertent fluid leakage may be particularly troublesome when an exact dose of drug is required for any particular treatment to be effective.

The screening device of the present disclosure is used determine whether the pre-filled syringes meet specific manufacturing specifications to ensure proper fit of the pre-filled syringes within the autoinjector devices. In particular, the screening devices are used for determining whether the stopper is positioned in the barrel falls within an acceptable tolerance prior to final assembly of the pre-filled syringe into the corresponding autoinjector device. The screening of pre-filled syringes ensures that only those pre-filled syringes that meet the requisite standards (i.e., syringes including stoppers positioned within the acceptable tolerance range) are passed along for final assembly with corresponding autoinjector devices, thereby reducing the risk of introducing a defective autoinjector into the market.

Figure 6:
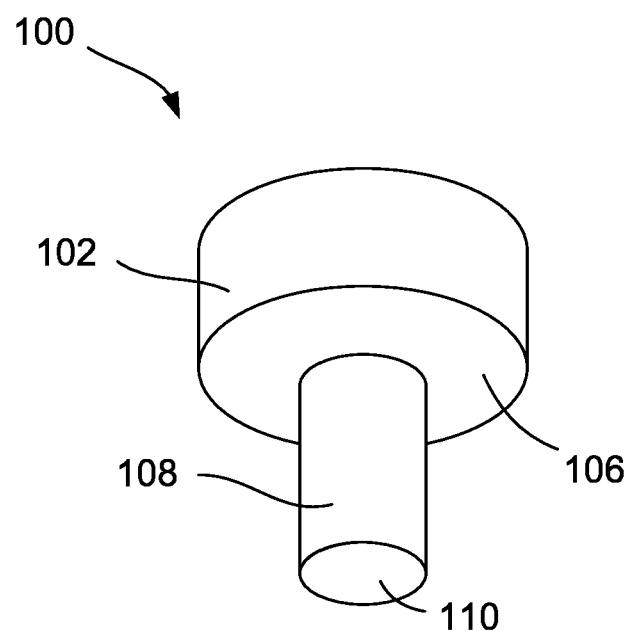
FIG. 6 is a perspective view of one embodiment of a screening device consistent with the present disclosure.
Figure 7:
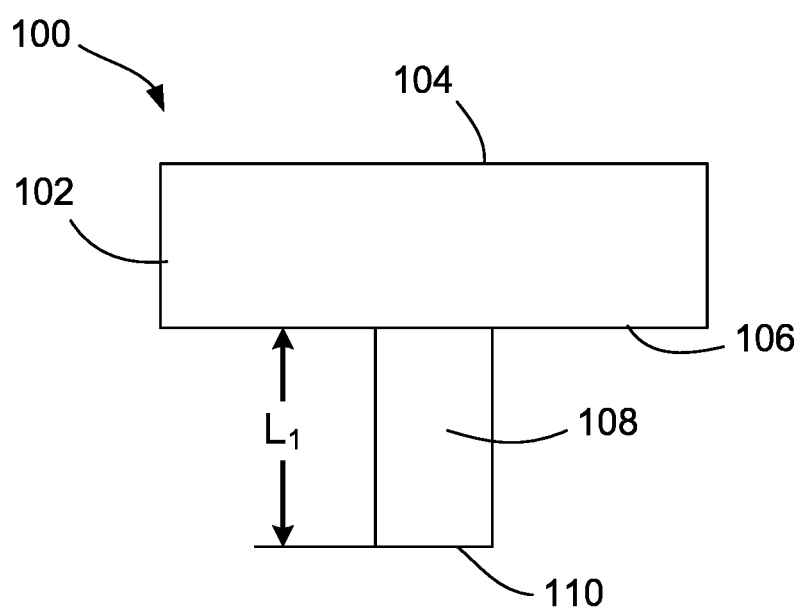
FIG. 7 is a side view of the screening device of FIG. 6.

FIGS. 6 and 7 are perspective and side views, respectively, of one embodiment of a screening device 100 consistent with the present disclosure. As shown, the screening device 100 generally comprises an upper member 102 including a top surface 104 and a bottom surface 106 and a lower member 108 extending from the bottom surface 106 of the upper member 102. The upper member 102 and the lower member 108 may each have a cylindrical shape, wherein the upper member 102 has a diameter greater than a diameter of the syringe barrel (see FIG. 8) while the lower member 108 has a diameter less than a diameter of the syringe barrel so as to allow the lower member to be inserted into an open proximal end of a pre-filled syringe barrel (shown in FIGS. 9A-9D. The lower member 108 of the screening device may be in a fixed position relative to the upper member 102 such that the upper and lower members 102, 108 are a single unit (i.e., the lower member 108 does not move relative to the upper member 108). For example, in some embodiments, the upper and lower members may be integrally formed with one another, while in other embodiments, the upper and lower members may be formed separately and then secured to one another in a fixed position via adhesive, ultrasonic welding, or the like. In such embodiments, the lower member 108 has a length $L_1$ measured from the bottom surface 106 of the upper member 102 to a distal end 110 of the lower member 108. The length $L_1$ of the lower member 108 is approximately equal to the predetermined minimum distance (i.e., specific distance D2 along a length of syringe barrel to which a plunger rod from a corresponding autoinjector device extends when the pre-filled syringe is loaded into the autoinjector).

Figure 8:
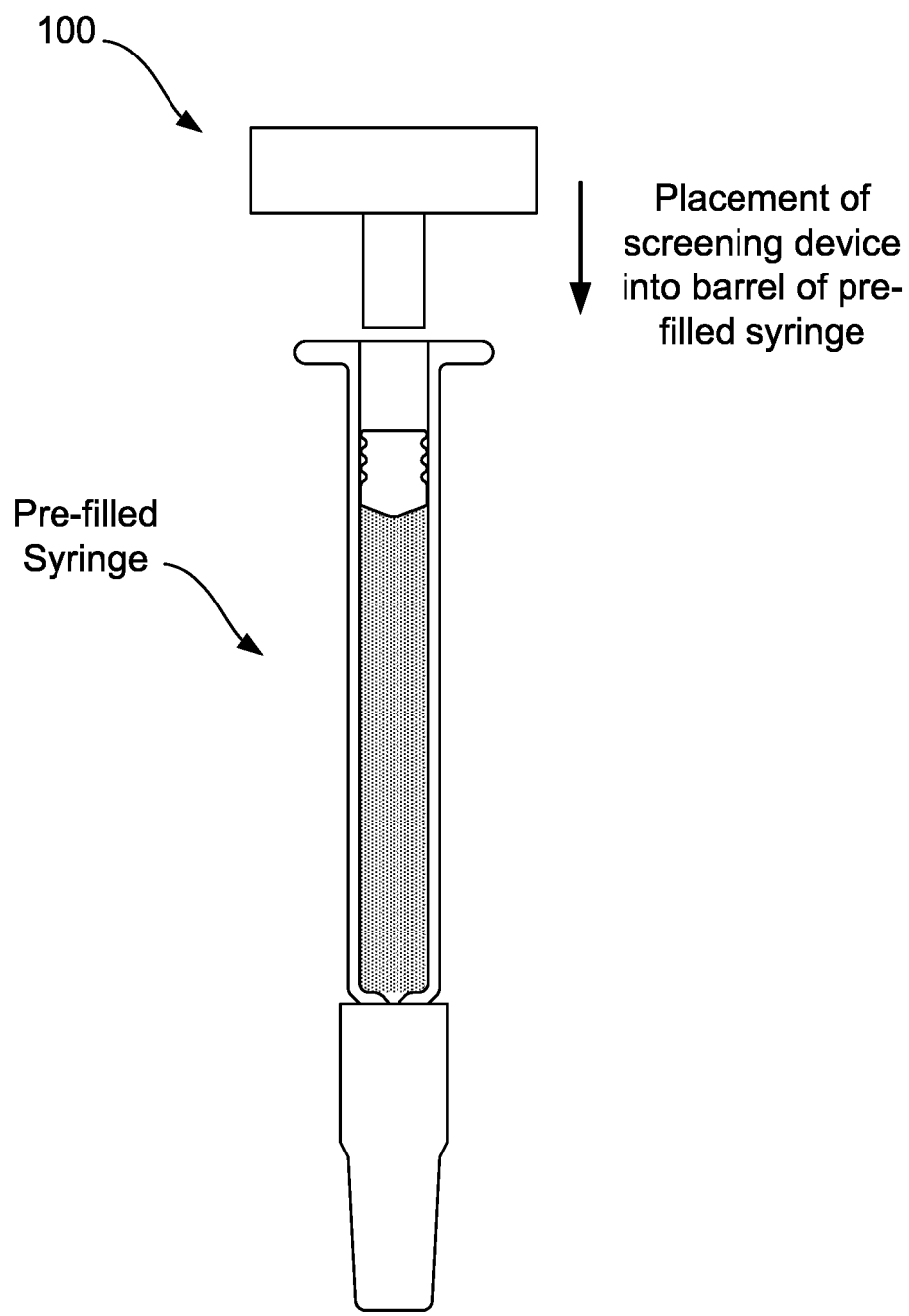
FIG. 8 is a side view, partly in section, illustrating placement of the screening device of FIG. 6 relative to a pre-filled syringe to undergo a screening procedure with the screening device.

FIG. 8 is a side view, partly in section, illustrating placement of the screening device 100 relative to a pre-filled syringe to undergo a screening procedure. FIG. 9A is an enlarged side view, partly in section, illustrating placement of the screening device 100 relative to an open proximal end of a pre-filled syringe. As shown, a screener (i.e., person utilizing the screening device 100 to screen pre-filled syringes) need only place the lower member 108 into the open proximal end of the syringe barrel to determine whether the pre-filled syringe passes or fails the screening procedure. In particular, placement of the screening device 100 within the open proximal end allows for determination of whether the stopper is positioned a minimum distance from the proximal end which dictates whether the pre-filled syringe passes or fails the screening.

FIGS. 9B-9D are enlarged side views, partly in section, illustrating passing and failing of the pre-filled syringe based on physical positioning of the screening device 100 as a result of the position of the stopper within the pre-filled syringe. For example, as a result of the length $L_1$ of the lower member 108 being approximately equal to the predetermined minimum distance, upon insertion of the lower member 108 into the open proximal end of a pre-filled syringe, the distal end 110 of the lower member 108 will either make contact with the stopper in the barrel or will not make contact with the stopper, thereby indicating whether the stopper position is below the minimum distance tolerance factor or is above (or at) the minimum distance tolerance factor.

For example, as shown in FIGS. 9B and 9C, in the event that the entire length of the lower member 108 is able to be received within the syringe barrel as a result of the stopper position being greater than (FIG. 9B) or just at (FIG. 9C) the minimum distance, then the upper member 102, specifically the bottom surface 106 will make contact and sit flush with the open proximal end, thereby providing a visual indication to the screener that the pre-filled syringe passes the screening procedure. In particular, the upper member 102, due to the larger diameter, is adapted to engage the open proximal end and abut a flange portion of the open proximal end of the syringe when the stopper position is above (or at) the minimum distance.

As shown in FIG. 9D, in the event that the distal end 110 of the lower member 108 makes contact with a stopper that is positioned below the minimum distance tolerance factor, the entire length $L_1$ of the lower member will be prevented from being received within the syringe barrel due to the resistance encountered from the stopper. In turn, the upper member 102 will sit proud relative to the open proximal end of the syringe barrel (i.e., the upper member will not make contact and sit flush with the open proximal end), thereby providing a visual indication to the screener that the pre-filled syringe fails the screening procedure and should be taken out of circulation to ensure that the defective pre-filled syringe is not passed on for subsequent loading into an autoinjector, which would otherwise result in a defective autoinjector.

In other embodiments, the screening device may include a movable lower member for providing visual pass/fail indication. For example, FIGS. 10, 11, and 12A-12B depict a screening device 200 including a movable lower member having a single visual indicator for providing pass/fail visual indication, while FIGS. 13, 14A-14B, and 15A-15B depict a screening device 300 including a movable lower member having a dual-visual indicator for providing pass/fail visual indication.

Figure 10:
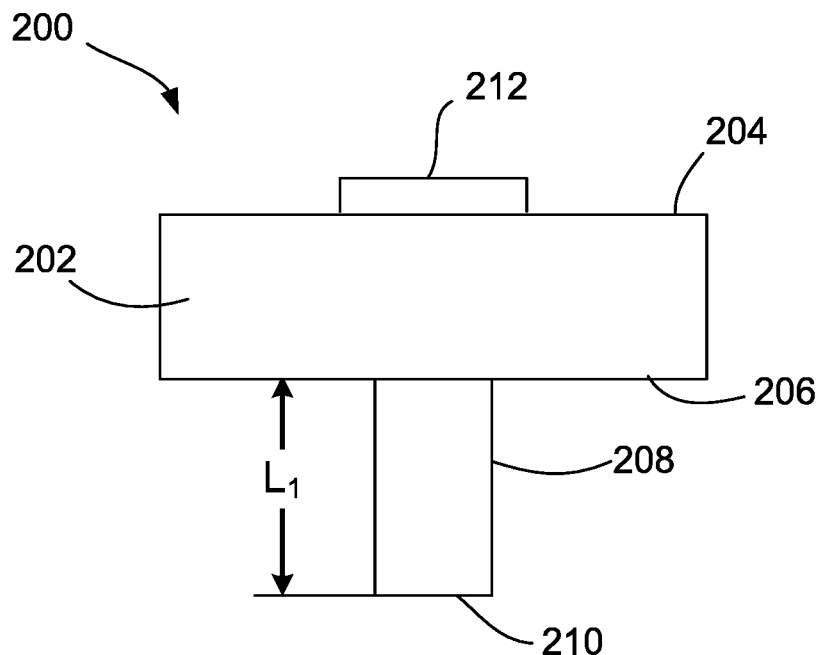
FIG. 10 is a side view of another embodiment of a screening device consistent with the present disclosure including a movable lower member having a single visual indicator for providing pass/fail visual indication.
Figure 11:
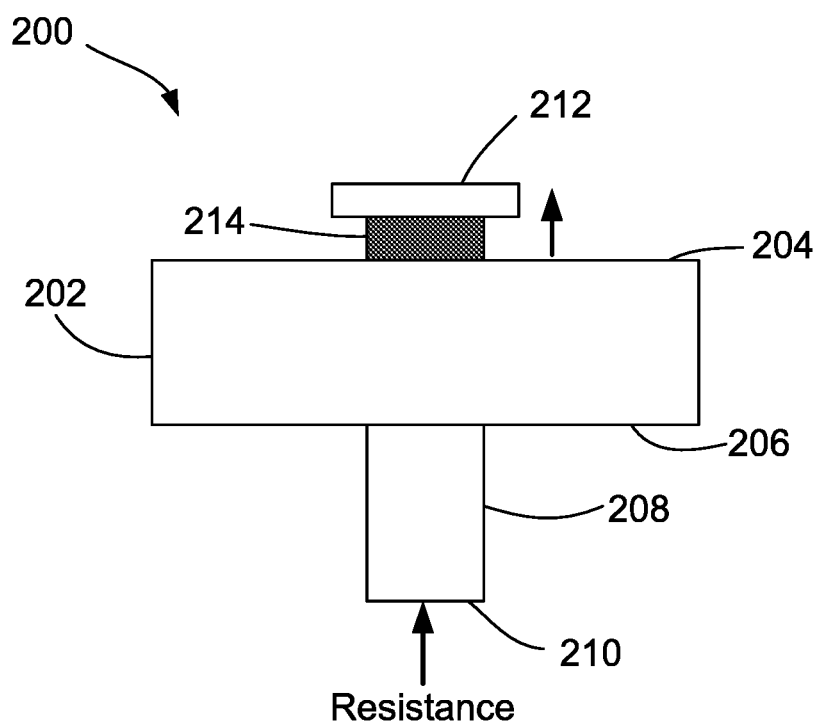
FIG. 11 is a side view of the screening device of FIG. 10 illustrating movement of a lower member to raise a flanged top to expose a visual indicator providing a pass/fail indication.

As shown in FIGS. 10 and 11, screening device 200 includes an upper member 202 including a top surface 204 and a bottom surface 206 and further including a central bore extending between the top and bottom surfaces 204, 206. The screening device 200 further includes a lower member 208 movably coupled to the upper member 202 such that the lower member 208 can move relative to the upper member 202 upon encountering resistance from the stopper when a screener inserts the lower member 208 into the syringe barrel. In particular, the lower member 208 includes an elongate body (i.e., a rod or pin) received within the central bore of the upper member 202, the body including a proximal end having a flanged top 212 adapted to rest upon the top surface 204 of the upper member 202 and maintain the lower member body within the central bore of the upper member 202 and an opposing distal end 210 for contacting the stopper during the screening procedure. The specific length $L_1$ of the lower member 208 (that extends from the bottom surface of the upper member) is approximately equal to the predetermined minimum distance tolerance factor.

The lower member 208 is configured to translate along a longitudinal axis of the upper member 202 between various positions that can provide a screener with visual indications as to whether the pre-filled syringe passes or fails the screening procedure. For example, screening device 200 can provide a visual indication to a screener as to whether the pre-filled syringe passes or fails the screening procedure simply based on whether the flanged top 212 remains flush against the top surface 204 of the upper member 202 or pops up and sits proud relative to the top surface 204 of the upper member 202. For example, in the illustrated embodiment, the screening device 200 includes a single visual indicator 214 (i.e., color, insignia, marking) provided along a length of the proximal end of the lower member 208, immediately adjacent to the flanged top 212, indicating failure of the screening procedure. For example, the single visual indicator 214 may be the color red or may have text reading "FAIL", or the like. The single visual indicator 214 is only visible to a screener if the flanged top 212 pops up and sits proud.

As a result of the length $L_1$ of the lower member 208 being approximately equal to the predetermined minimum distance, upon insertion of the lower member 208 into the open proximal end of a pre-filled syringe, the distal end 210 of the lower member 208 will either make contact with the stopper in the barrel or will not make contact with the stopper, thereby indicating whether the stopper position is below the minimum distance tolerance factor or is above (or at) the minimum distance tolerance factor.

Figure 12B:
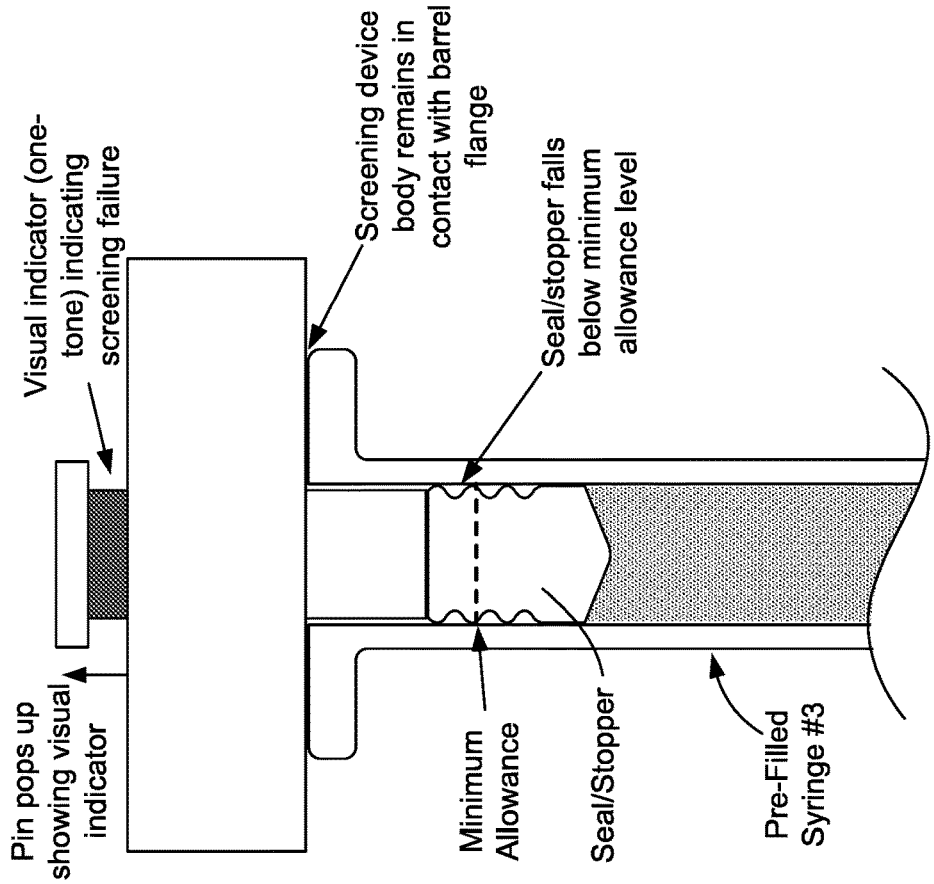
FIGS. 12A and 12B are enlarged side views, partly in section, illustrating passing and failing of the pre-filled syringe based on positioning of the flanged top of the movable lower member of the screening device as a result of the position of the stopper within the pre-filled syringe.
Figure 12A:
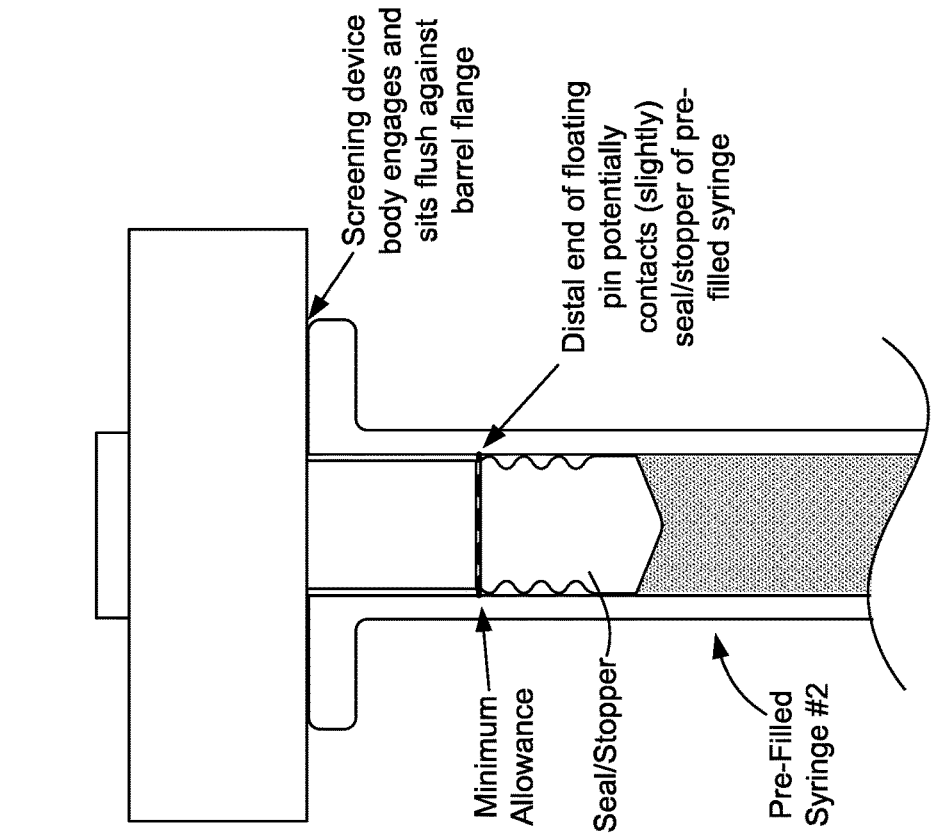

For example, as shown in FIG. 12A, in the event that the entire length of the lower member 208 is able to be received within the syringe barrel as a result of the stopper position being at or greater than the minimum distance, then the flanged top 212 will remain flush with the top surface 204 of the upper member 202, thereby indicating to the screener that the pre-filled syringe passes the screening procedure. As shown in FIG. 12B, in the event that the distal end 210 of the lower member 208 makes contact with a stopper that is positioned below the minimum distance tolerance factor, then the resistance encountered from the stopper will cause the lower member 208 to translate relative to the upper member 202, thereby causing the flanged top 212 to sit proud relative to the top surface 204 of the upper member 202 and exposing the single visual indicator 214 to indicate failure. It should be noted that, in either case of pass or fail illustrated in FIGS. 12A and 12B, the upper member 202, specifically the bottom surface 206 will make contact and sit flush with the open proximal end of the barrel, as it is only the lower member 208 that moves in response to any resistance from the stopper. It should be noted that, in such embodiments, the screening device, particularly the lower member 208, includes a relatively lightweight material (e.g., lightweight plastic) to ensure that the lower member 208 does not move the stopper from its position in the barrel.

Figure 13:
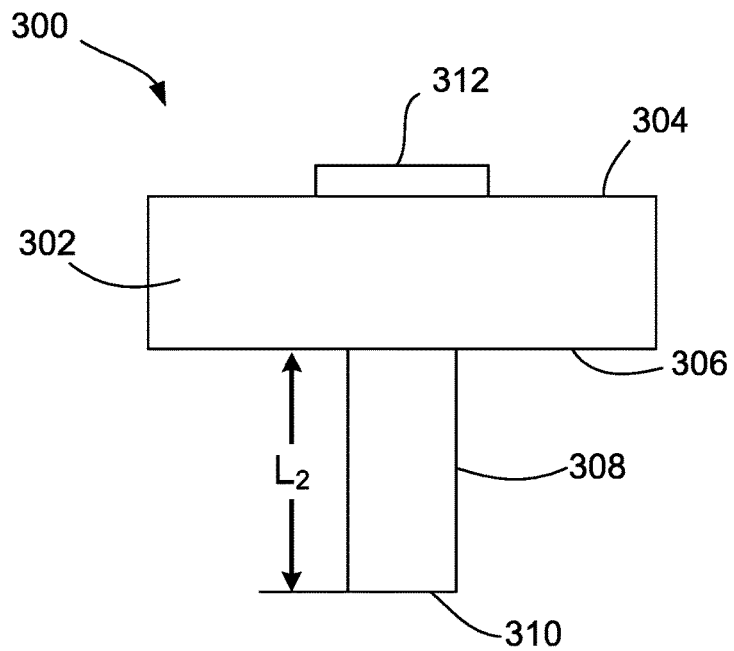
FIG. 13 is a side view of another embodiment of a screening device consistent with the present disclosure including a movable lower member having a dual-visual indicator for providing pass/fail visual indication.

FIG. 13 is a side view of a screening device 300 including a movable lower member having a dual-visual indicator for providing pass/fail visual indication. The screening device 300 is similar to the screening device 200 previously described herein. In particular, the screening device 300 includes an upper member 300 including a top surface 304 and a bottom surface 306 and further including a central bore extending between the top and bottom surfaces 304, 306.

The screening device 300 further includes a lower member 308 movably coupled to the upper member 302 such that the lower member 308 can move relative to the upper member 302 upon encountering resistance from the stopper when a screener inserts the lower member 308 into the syringe barrel. In particular, the lower member 308 includes an elongate body (i.e., a rod or pin) received within the central bore of the upper member 302, the body including a proximal end having a flanged top 312 adapted to rest upon the top surface 304 of the upper member 302 and maintain the lower member body within the central bore of the upper member 302 and an opposing distal end 310 for contacting the stopper during the screening procedure.

The lower member 308 is configured to translate along a longitudinal axis of the upper member 302 between various positions that can provide a screener with visual indications as to whether the pre-filled syringe passes or fails the screening procedure. For example, screening device 300 includes two visual indicators provided along a length of the proximal end of the lower member 308, including a first visual indicator 314 immediately adjacent to the flanged top 312 and indicating passing of the screening procedure, and a second visual indicator 316 adjacent to the first visual indicator and indicating failure of the screening procedure. For example, the first visual indicator 314 may be the color green and/or may have text reading "PASS", or the like, while the second visual indicator 316 may be the color red and/or may have text reading "FAIL".

Figure 14A:
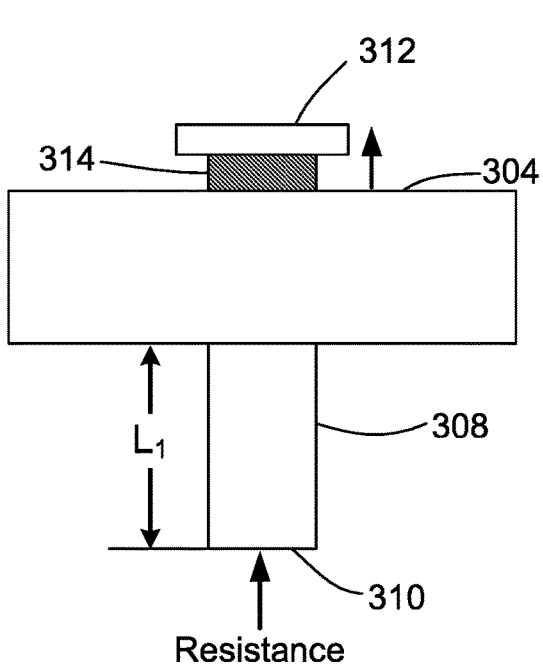
FIGS. 14A and 14B are enlarged side views of the screening device of FIG. 13 illustrating movement of the flanged top of the lower member to expose a first visual indicator (pass) and a second visual indicator (fail).
Figure 14B:
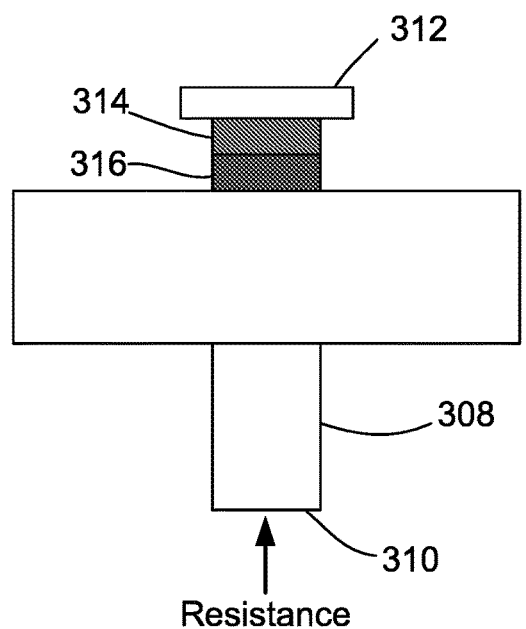

Due to the two visual indicators 314, 316, the specific length L2 of the lower member 308 body (that extends from the bottom surface 306 of the upper member 302 when the flanged top 312 is completely flush with the top surface 304 of the upper member 302) is greater than the predetermined minimum distance so as to account for a length of the first visual indicator 314 provided on the proximal end of the lower member and allow the flanged top 312 to sit proud and expose the first visual indicator 314 to indicate passage of the pre-filled syringe. For example, unlike other embodiments in which a flanged top sitting flush with the upper member indicates passing of the pre-filled syringe (as is the case with screening device 200), the two-indicator screening device 300 requires the flanged top 312 to sit proud to expose the first visual indicator 314 to indicate passing of the pre-filled syringe, as shown in FIG. 14A. When the flanged top 312 is sitting proud and exposing only the first visual indicator 314, the length $L_1$ of the lower member 308 that extends from the bottom surface 306 of the upper member is approximately equal to or greater than the minimum distance tolerance factor, indicating that the stopper is positioned at or above the minimum distance. In the event that the stopper is positioned below the minimum distance, the flanged top 312 will continue to rise to then expose the second visual indictor 316 to indicate failure, as shown in FIG. 14B.

Figure 15B:
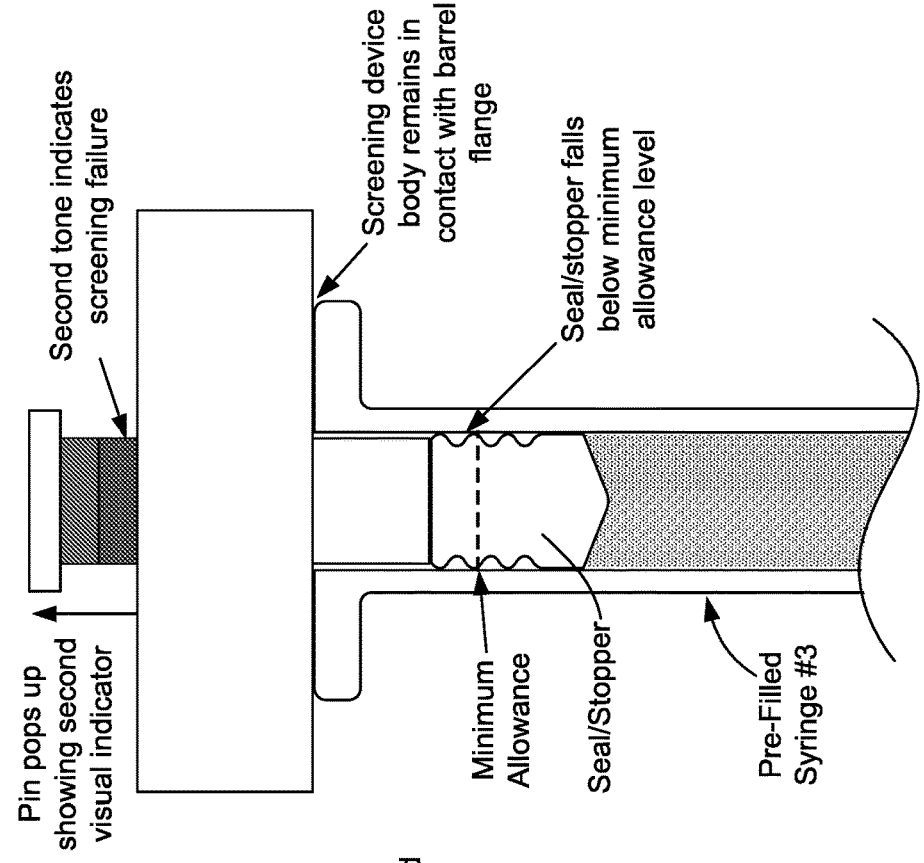
FIGS. 15A and 15B are enlarged side views, partly in section, illustrating passing and failing of the pre-filled syringe based on positioning of the flanged top of the movable lower member of the screening device of FIG. 13 as a result of the position of the stopper within the pre-filled syringe.
Figure 15A:
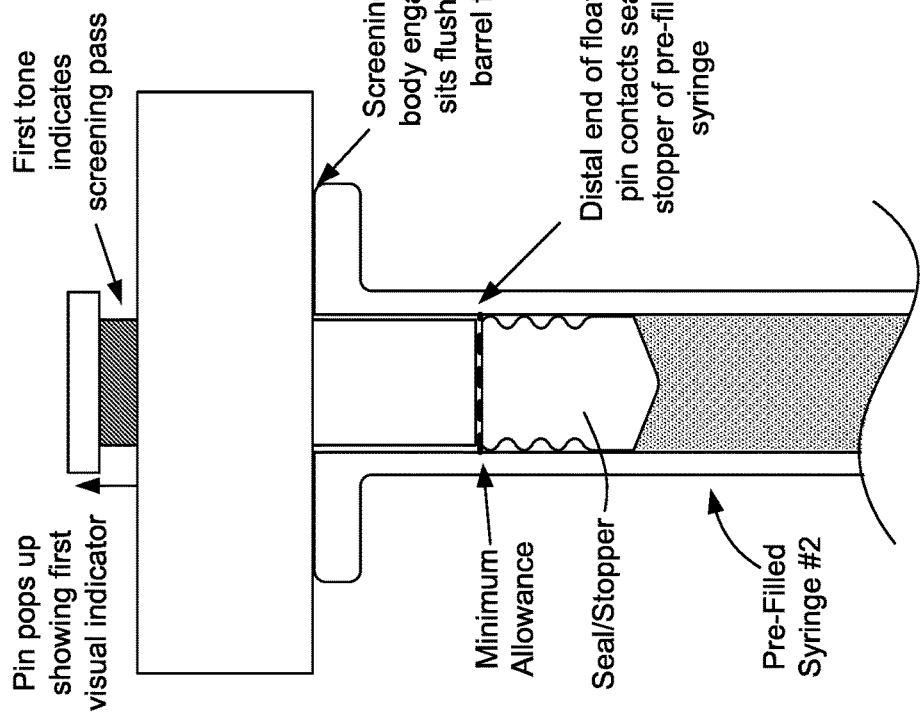

For example, as shown in FIG. 15A, in the event that the distal end 310 of the lower member 308 contacts a stopper that is positioned at or above the minimum distance tolerance factor, the lower member 308 translates relative to the upper member 302 (which is abutting the open proximal end of the syringe barrel), thereby causing the flanged top 312 to sit proud relative to the top surface 304 of the upper member 302 and expose the first visual indicator 314 to indicate that the pre-filled syringe passes the screening procedure. As shown in FIG. 15B, in the event that the stopper is positioned below the minimum distance tolerance factor, the lower member 308 will continue to translate towards the upper member 302, such that the flanged top 312 will continue to rise to then expose the second visual indictor 316 to indicate failure.

Accordingly, the screening devices of the present disclosure provide a relatively simple, yet effective design for determining proper placement of stoppers in a plurality of pre-filled syringes to ensure that only those pre-filled syringes that meet the requisite standards (i.e., syringes having stoppers positioned within the acceptable tolerance range) are passed along for final assembly with corresponding autoinjector devices, thereby reducing the risk of introducing a defective autoinjector into the market.

Reference throughout this specification to "one embodiment" or "an embodiment" means that a particular feature, structure, or characteristic described in connection with the embodiment is included in at least one embodiment. Thus, appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

The terms and expressions which have been employed herein are used as terms of description and not of limitation, and there is no intention, in the use of such terms and expressions, of excluding any equivalents of the features shown and described (or portions thereof), and it is recognized that various modifications are possible within the scope of the claims. Accordingly, the claims are intended to cover all such equivalents.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

Various modifications of the invention and many further embodiments thereof, in addition to those shown and described herein, will become apparent to those skilled in the art from the full contents of this document, including references to the scientific and patent literature cited herein. The subject matter herein contains important information, exemplification and guidance that can be adapted to the practice of this invention in its various embodiments and equivalents thereof.

What is claimed is:

1. A method comprising:
   inserting a lower member of a screening device into a first barrel of a first pre-filled syringe, the lower member being coupled to an upper member of the screening device and being shaped or sized to be received through syringe barrels of a plurality of pre-filled syringes for determination of a stopper position within the syringe barrels, wherein at least a portion of the lower member extends from a bottom surface of the upper member, and wherein the lower member comprises a proximal end including a flanged top configured to rest upon a top surface of the upper member prior to insertion into the syringe barrels of the plurality of pre-filled syringes;
   advancing the screening device into the first pre-filled syringe until the upper member contacts a first top of the first pre-filled syringe; and
   identifying the first pre-filled syringe as failing inspection in response to the proximal end of the flanged top of the lower member moving beyond a predetermined distance from the top surface of the upper member.

2. The method of claim 1 further comprising:
   inserting the lower member of the screening device into a second barrel of a second pre-filled syringe;
   advancing the screening device into the second pre-filled syringe until the upper member contacts a second top of the second pre-filled syringe; and
   identifying the second pre-filled syringe as passing inspection in response to the proximal end of the flanged top of the lower member remaining flush with the top surface of the upper member or remaining within the predetermined distance from the top surface of the upper member.

3. The method of claim 1, wherein the lower member comprises a first visual indicator defined along a length of the proximal end of the lower member immediately adjacent to the flanged top, and wherein the predetermined distance from the top surface of the upper member is indicated by the first visual indicator.

4. The method of claim 1, wherein the predetermined distance corresponds to a tolerance factor comprising a minimum distance limit for the stopper position within the syringe barrels of the plurality of pre-filled syringes.

5. The method of claim 1, wherein a length of the lower member extending from the bottom surface of the upper member, when the flanged top is abutting the top surface of the upper member, is approximately equal to the predetermined distance.

6. The method of claim 1, wherein the predetermined distance is approximately 8.00 mm.

7. The method of claim 1, wherein the predetermined distance is approximately 8.46 mm.

* * * * *